United States Patent
Rising

(10) Patent No.: US 6,268,913 B1
(45) Date of Patent: Jul. 31, 2001

(54) METHOD AND COMBUSTOR APPARATUS FOR SENSING THE LEVEL OF A CONTAMINANT WITHIN A COMBUSTION FLAME

(75) Inventor: Bruce Rising, Oviedo, FL (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 0 days.

(21) Appl. No.: 09/258,561

(22) Filed: Feb. 26, 1999

(51) Int. Cl.[7] .................................................. G01J 3/28
(52) U.S. Cl. ............................. 356/326; 356/328
(58) Field of Search ......................... 356/326, 328; 431/18, 21

(56) References Cited

U.S. PATENT DOCUMENTS

| | | | |
|---|---|---|---|
| 3,938,888 | 2/1976 | Folsom et al. | 356/87 |
| 4,234,257 | 11/1980 | Carter et al. | 356/417 |
| 4,404,841 | * 9/1983 | Franke et al. | 73/35 |
| 4,810,680 | 3/1989 | Bickford et al. | 501/103 |
| 4,820,046 | 4/1989 | Sohma et al. | 356/328 |
| 4,830,601 | * 5/1989 | Dahlander et al. | 431/12 |
| 4,896,965 | 1/1990 | Goff et al. | 356/417 |
| 4,973,159 | 11/1990 | Sohma et al. | 356/328 |
| 4,983,853 | 1/1991 | Davall et al. | 250/554 |
| 5,131,746 | 7/1992 | O'Rourke et al. | 356/319 |
| 5,164,600 | 11/1992 | Das et al. | 250/554 |
| 5,316,955 | 5/1994 | Govorchin | 436/155 |
| 5,361,586 | 11/1994 | McWhirter et al. | 60/737 |
| 5,397,442 | 3/1995 | Wachsman | 204/153.16 |
| 5,432,090 | 7/1995 | Tanaka et al. | 436/79 |
| 5,446,125 | 8/1995 | Honda et al. | 528/486 |
| 5,618,433 | 4/1997 | Tarbet et al. | 210/634 |
| 5,706,092 | 1/1998 | Stannard et al. | 356/416 |
| 5,741,711 | 4/1998 | Amirav et al. | 436/154 |
| 5,763,888 | 6/1998 | Glasheen et al. | 250/372 |
| 5,857,320 | 1/1999 | Amos et al. | 60/39.06 |

* cited by examiner

Primary Examiner—Robert H. Kim
Assistant Examiner—Zandra V. Smith
(74) Attorney, Agent, or Firm—Eckert Seamans Cherin & Mellott, LLC

(57) ABSTRACT

A gas turbine combustor burns fuel from a fuel supply. The combustor includes a combustion chamber and a fuel delivery system for delivering the fuel to the combustion chamber. A pilot or fuel nozzle establishes a combustion flame in the combustion chamber by burning the fuel. One or more fuel lines operatively connect the fuel delivery system to the fuel supply. A flame spectrometer senses the level, such as the concentration level, of a fuel contaminant, such as sodium, within the combustion flame. A control system disables the fuel delivery system as a function of the contaminant's concentration level or accumulated concentration level.

21 Claims, 4 Drawing Sheets

METHOD AND COMBUSTOR APPARATUS FOR SENSING THE LEVEL OF A CONTAMINANT WITHIN A COMBUSTION FLAME

BACKGROUND OF THE INVENTION

1. Field of the Invention

This invention relates to a combustor for burning fuel and, more specifically, to a combustor, such as a gas turbine combustor, for burning fuel and compressed air, and sensing the level of a contaminant, such as sodium, within the combustion flame. The invention also relates to a method for burning fuel and sensing the level of a contaminant within the combustion flame.

2. Background Information

In a gas turbine, fuel is burned with compressed air, produced by a compressor. The combustion reaction takes place in one or more combustors. An example of such a combustor is disclosed in U.S. Pat. No. 5,361,586, which is incorporated by reference herein.

Substantial costs may arise due to corrosion of hot-section components of the gas turbine, including the combustors. Sodium, for example, is an extremely corrosive contaminant, even in small concentrations, to any hot-section component in the gas turbine.

Currently, fuel contaminants are typically identified by random, periodic fuel sampling. This requires both a technician, who is skilled in laboratory analysis, and a relatively expensive atomic emission spectrometer. However, problems may result due to the periodic nature of the sampling. For example, during periods when no fuel is sampled, it is possible for salt water (i.e., containing sodium) to contaminate the fuel, enter into the combustor, and initiate hot corrosion thereof.

It is, therefore, desirable to provide a combustor with a non-obtrusive, economical, real-time, contaminant sensing function.

SUMMARY OF THE INVENTION

This need and others are satisfied by the invention which is directed to a combustor which senses the level of a contaminant within the combustion flame, and disables fuel delivery to the combustor as a function of the contaminant level.

As one aspect of the invention, a combustor for burning fuel comprises a combustion chamber; means for delivering the fuel to the combustion chamber; means for establishing a combustion flame in the combustion chamber by burning the fuel; at least one fuel line operatively connecting the means for delivering to a fuel supply; means for sensing a level of a contaminant within the combustion flame; and means for disabling the means for delivering as a function of the level of the contaminant.

The contaminant may be sodium, the combustion flame may include ionized sodium, and the means for sensing may include means for sensing the level of the ionized sodium in the combustion flame. As a refinement, the combustion flame has a spectrum, and the means for sensing the level of the contaminant includes spectrometer means for monitoring the spectrum of the combustion flame.

Preferably, the means for disabling includes means for storing the accumulation of a concentration level of the contaminant with respect to operating time of the combustor, and means for displaying the accumulation of the concentration level.

As another aspect of the invention, a gas turbine combustor for burning fuel comprises a combustion chamber; means for delivering the fuel to the combustion chamber; means for establishing a combustion flame having a combustion spectrum in the combustion chamber by burning the fuel with compressed air; at least one fuel line operatively connecting the means for delivering to a fuel supply; means employing the combustion spectrum of the combustion flame for sensing a level of a contaminant; and means for disabling the means for delivering as a function of the level of the contaminant.

As a further aspect of the invention, a method for burning fuel in a combustor comprises employing a combustion chamber; delivering the fuel to the combustion chamber; establishing a combustion flame in the combustion chamber by burning the fuel; sensing a level of a contaminant within the combustion flame; and stopping delivery of the fuel to the combustion chamber as a function of the level of the contaminant.

Preferably, the method further comprises storing an historical record of an accumulation of a concentration level of the contaminant with respect to operating time of the combustor; and displaying the historical record.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

As employed herein, the term "combustor" shall expressly include, but not be limited to, any combustion system in which a fuel is introduced and burned, such as, for example, internal or external combustion systems which produce a flame, a combustion turbine, a gas turbine combustor, a jet engine combustor, intermittent combustion systems such as a reciprocating engine, a boiler, an internal combustion engine, or any other heat engine.

As employed herein, the term "combustion chamber" shall expressly include, but not be limited to, the chamber or zone in which combustion occurs, such as, for example, the cylinder of a reciprocating engine; the single annular chamber or individual chambers of a gas turbine combustor; the combustion zone of a ramjet duct; the chamber, with a single venturi outlet, of a rocket; the space in a boiler furnace in which combustion of gaseous products from the fuel takes place; the space in an internal combustion engine above the piston in which combustion occurs; or any open or closed flame.

As employed herein, the term "spectrometer" shall expressly include, but not be limited to, any device for measuring the wavelength, energy distribution, or emission spectrum from a radiating source, such as a combustion flame.

Figure 1:
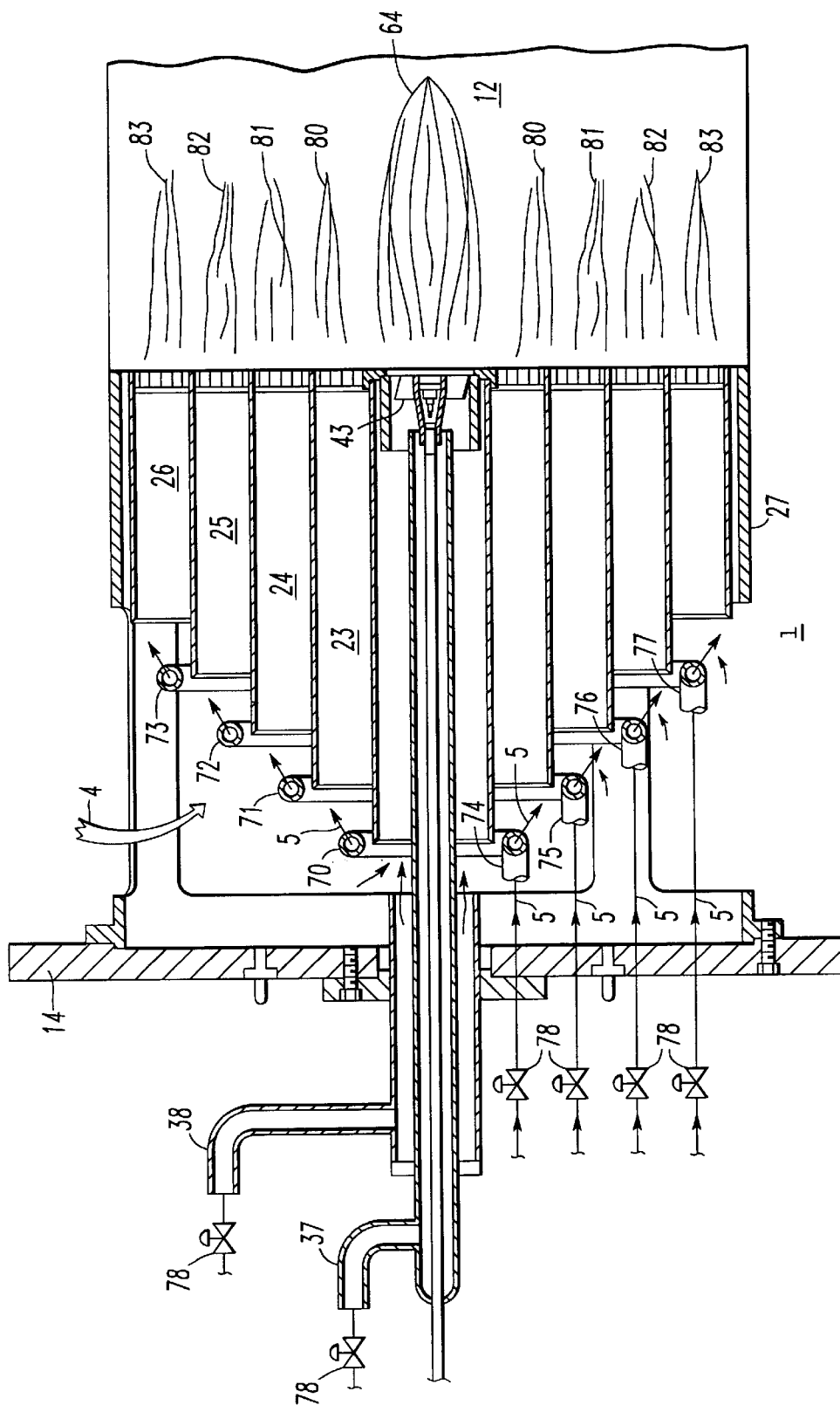
FIG. 1 is a longitudinal cross-section through the front portion of a combustor.

Referring to FIG. 1, wherein like reference numerals refer to like elements, a combustor 1 of a gas turbine as disclosed in U.S. Pat. No. 5,361,586 is illustrated. As more fully disclosed in U.S. Pat. No. 5,361,586, the combustor 1 has fuel/air premixing passages 23–26 with inlet ends and outlet ends. The fuel/air premixing passages 23–26 premix air, such as compressed air 4, with fuel 5 delivered via toroidal manifolds 7073 disposed upstream of the inlet ends of those passages.

The manifolds 70–73 are supplied with fuel 5 via fuel lines 74–77. Each of these fuel lines has a fuel flow control valve 78 for adjusting the flow of fuel to the manifolds 70–73 and fuel pipes 37,38 of the combustor 1. The fuel/air premixing passages 23–26 and the manifolds 70–73 have a combustor liner 27 disposed therearound. The combustor liner 27 connects to a plate 14 forming a sealed upstream end.

In the combustion zone 12, fuel/air mixtures are ignited by a pilot flame 64 of a pilot fuel/air swirler 43, thereby creating concentric flame fronts 80–83 within the combustion zone 12 that surround the pilot flame 64.

Figure 2:
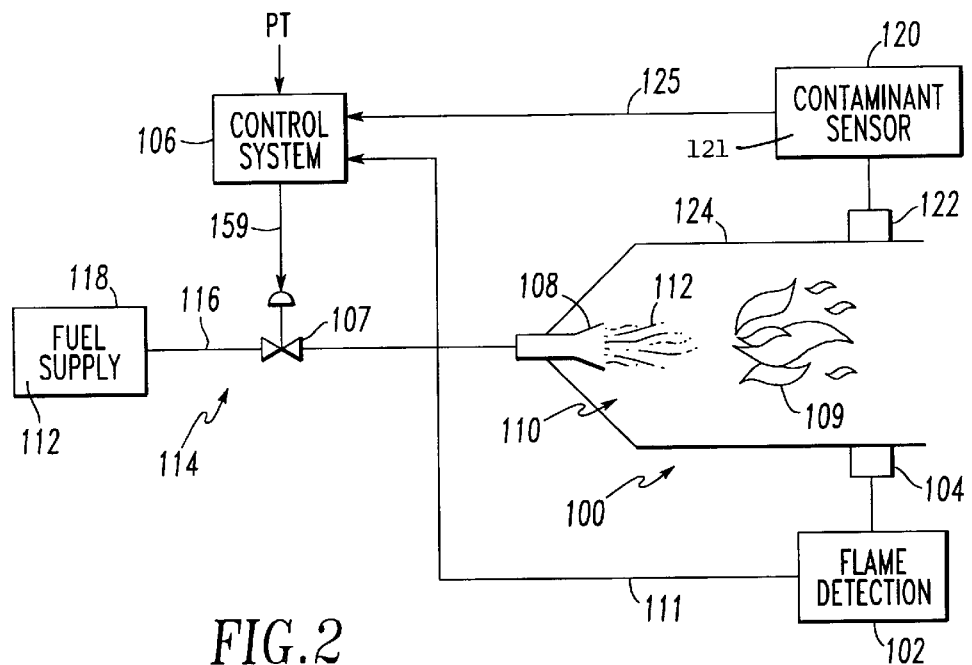
FIG. 2 is a block diagram of one embodiment of a combustor including a fuel contaminant sensor in accordance with the invention.

Referring to FIG. 2, an exemplary gas turbine combustor 100 is installed with a suitable flame detection system 102. For purpose of illustration, but not limitation, the invention is described herein in connection with exemplary gas turbine combustors, although the invention is applicable to a wide range of combustors which may or may not employ a flame detection system.

The exemplary flame detection system 102 comprises one or more optical flame detectors, such as detector 104, and a control system 106. Preferably, the exemplary control system 106 is integrated with a turbine control system (not shown) that controls the operation of a gas turbine (not shown). The control system 106 is connected to one or more fuel flow control valves, such as valve 107, in order to open, adjust, and/or close these valves to control the flow of fuel 112 to fuel nozzle 108. In turn, a combustion flame 109 is established in combustion chamber 124 by burning the fuel 112 in the presence of air 110. Upon the flame detection system 102 detecting loss of the combustion flame 109, signal 111 is output. In response to the signal 111, the control system 106 closes the valve 107. Once the valve 107 is closed, fuel 112 is no longer delivered to the combustion chamber 124 by fuel delivery system 114. That system 114 has a fuel line 116 which operatively connects the fuel supply 118 to the valve 107 and to the combustor 100. Without the delivery of the fuel 112, combustion is arrested.

A contaminant sensor 120 includes a spectrometer or spectrophotometer 121 having a suitable detector 122 to monitor for the presence of contaminants (e.g., metal, such as sodium). The detector 122 monitors flame radiation from contaminants within the flame 109 of the combustion chamber 124 during the combustion process. In the exemplary embodiment, the detector 122 is a photoelectric detector or photo-detector, which is wavelength specific and optimized to detect the flame emission spectrum of specific trace metal contaminants, such as ionized sodium, in the flame 109.

Sodium, for example, produces a unique, and intense, emission spectra as it burns. Sodium may result, for example, from salt water present in the fuel 112 or from salt spray. The presence of sodium in the flame 109 has a unique spectral characteristic (e.g., having a sodium "D" line emission at a wavelength of about 588.9 nm) which makes detection possible with the detector 122. The high temperatures inside the combustion chamber 124 produce enhanced radiation in the flame 109. Because sodium produces an intense spectra, and is one of the most corrosive substances, a sodium detector is preferably employed by the combustor 100 to detect the ionized sodium in the combustion spectrum.

As discussed below in connection with FIGS. 4 and 5, the contaminant sensor 120 can integrate with the control system 106 to sense the level 125 of a contaminant, such as sodium, from the combustion spectrum of the flame 109. In turn, the control system 106 disables the fuel delivery system 114 as a function of the level 125 to, thereby, arrest combustion whenever contaminant levels are too high.

Figure 3:
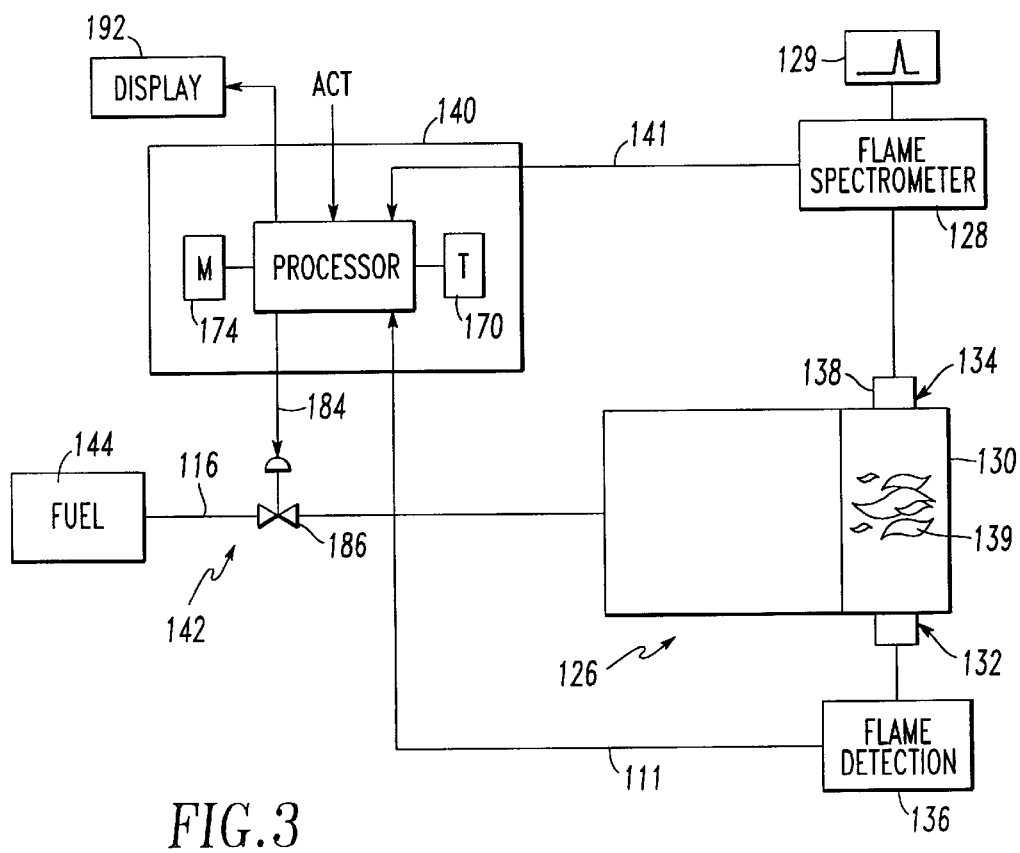
FIG. 3 is a block diagram of another embodiment of a combustor including a fuel contaminant sensor or in accordance with the invention.

Referring to FIG. 3, another exemplary combustor 126 is illustrated. In this embodiment, a flame spectrometer, such as a spectrographic scanning device 128, is employed to monitor the unique spectral characteristics of trace sodium in the combustor fuel during the combustion process. Preferably, the flame spectrometer 128 monitors the intense sodium "D" line emission 129 produced during the combustion process.

The combustor 126 includes a combustion chamber 130 having a plurality of flame detector ports 132,134 and a flame detection system 136. The flame spectrometer 128 has a suitable detector 138 mounted in the flame detector port 134. The detector 138 is employed to monitor the combustion spectrum of combustion flame 139 in the combustion chamber 130. Preferably, the flame spectrometer 128 detects the sodium "D" line emission 129 of sodium in the combustion flame 139.

As discussed below in connection with FIGS. 4 and 5, the flame spectrometer 128 cooperates with turbine control system 140 to sense the level 141 of a contaminant, such as sodium, from the combustion spectrum of the combustion flame 139. In turn, the control system 140 disables fuel delivery system 142 as a function of the level 141 to, thereby, arrest combustion whenever contaminant levels are too high.

Figure 4:
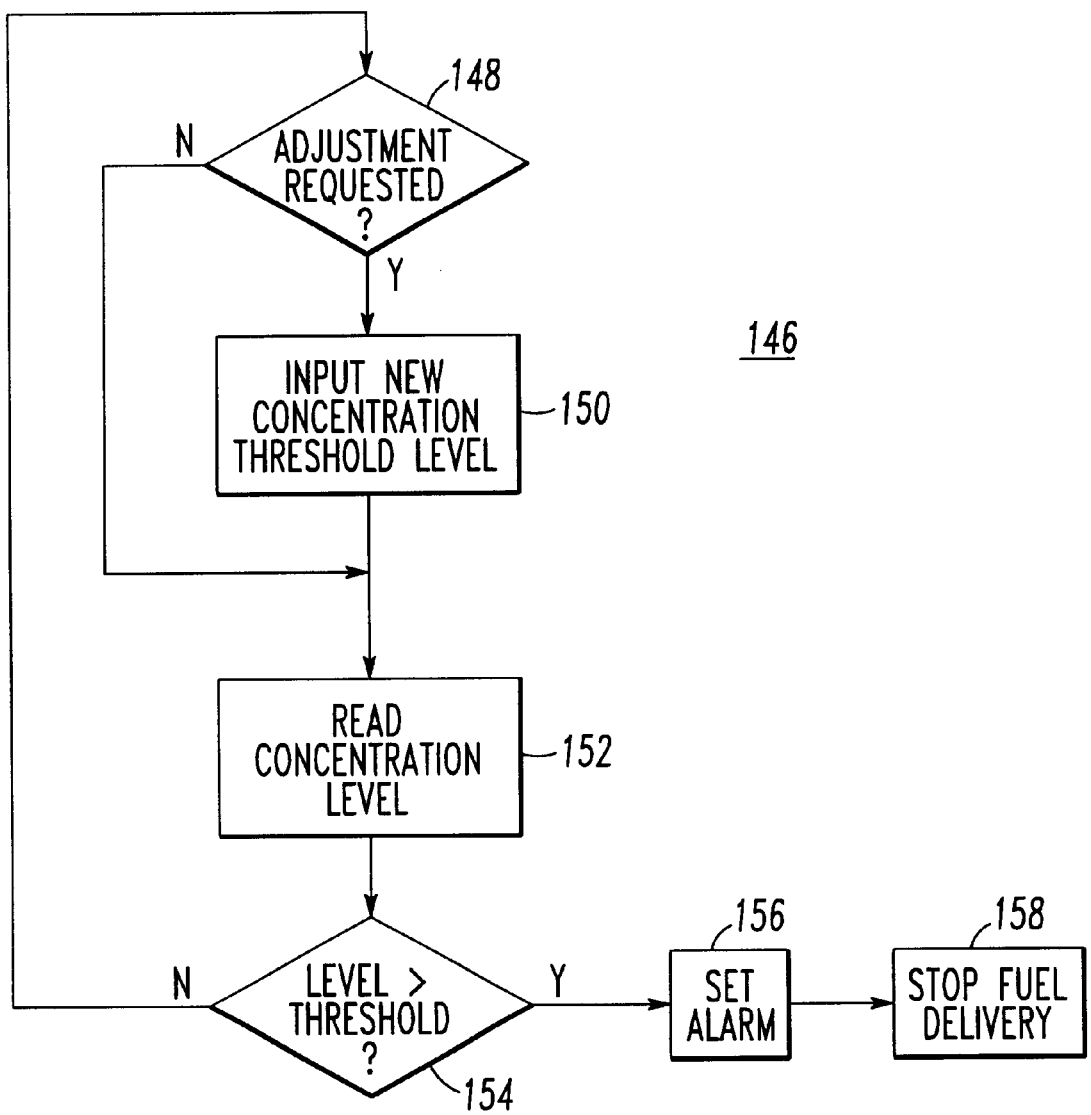
FIG. 4 is a flowchart of one embodiment of software suitable for execution by the control systems of FIGS. 2 and 3.

Referring to FIG. 4, an exemplary software routine 146 for execution by the control systems 106 and 140 of FIGS. 2 and 3, respectively, is illustrated. Although processor-based control systems 106,140 are shown, the invention is also applicable to a wide range of control devices (e.g., analog control systems, digital control systems, hybrid control systems). The routine 146 obtains a concentration level (e.g., ppm of ionized sodium in the combustion flame) of the contaminant from the corresponding contaminant sensor and, then, compares the concentration level to a predetermined (e.g., PT of FIG. 2) or suitably adjusted concentration threshold level (e.g., maximum allowed ppm of ionized sodium). Then, the result of the comparison is employed to determine whether to disable the corresponding fuel delivery system and, thus, arrest combustion.

For convenience of reference, the routine 146 of FIG. 4 is described with respect to the control system 106 of FIG. 2, although it is also applicable to the control system 140 of FIG. 3. First, at 148, it is determined whether an adjustment of the concentration threshold level has been requested by the user. If so, at 150, the user suitably inputs a new concentration threshold level. Otherwise, if no adjustment was requested, and after 150, the concentration level 125 is read, at 152, from the contaminant sensor 120. Then, at 154, the contaminant concentration level is compared to the threshold level. If the concentration level exceeds the threshold level, then, at 156, an alarm is generated. Next, at 158, output signal 159 is set to close the valve 107 and, thereby, stop delivery of the fuel 112. Otherwise, after 154, execution resumes at 148.

By employing the exemplary sodium detector 122 mounted directly to the combustor 100, all of the burning fuel 112 can be continuously screened, in real-time, for the presence of sodium. When the presence of sodium is detected, the alarm is generated and is employed to shut-down the combustor 100, thereby reducing the risk of corrosion and subsequent damage to the combustor 100.

Figure 5:
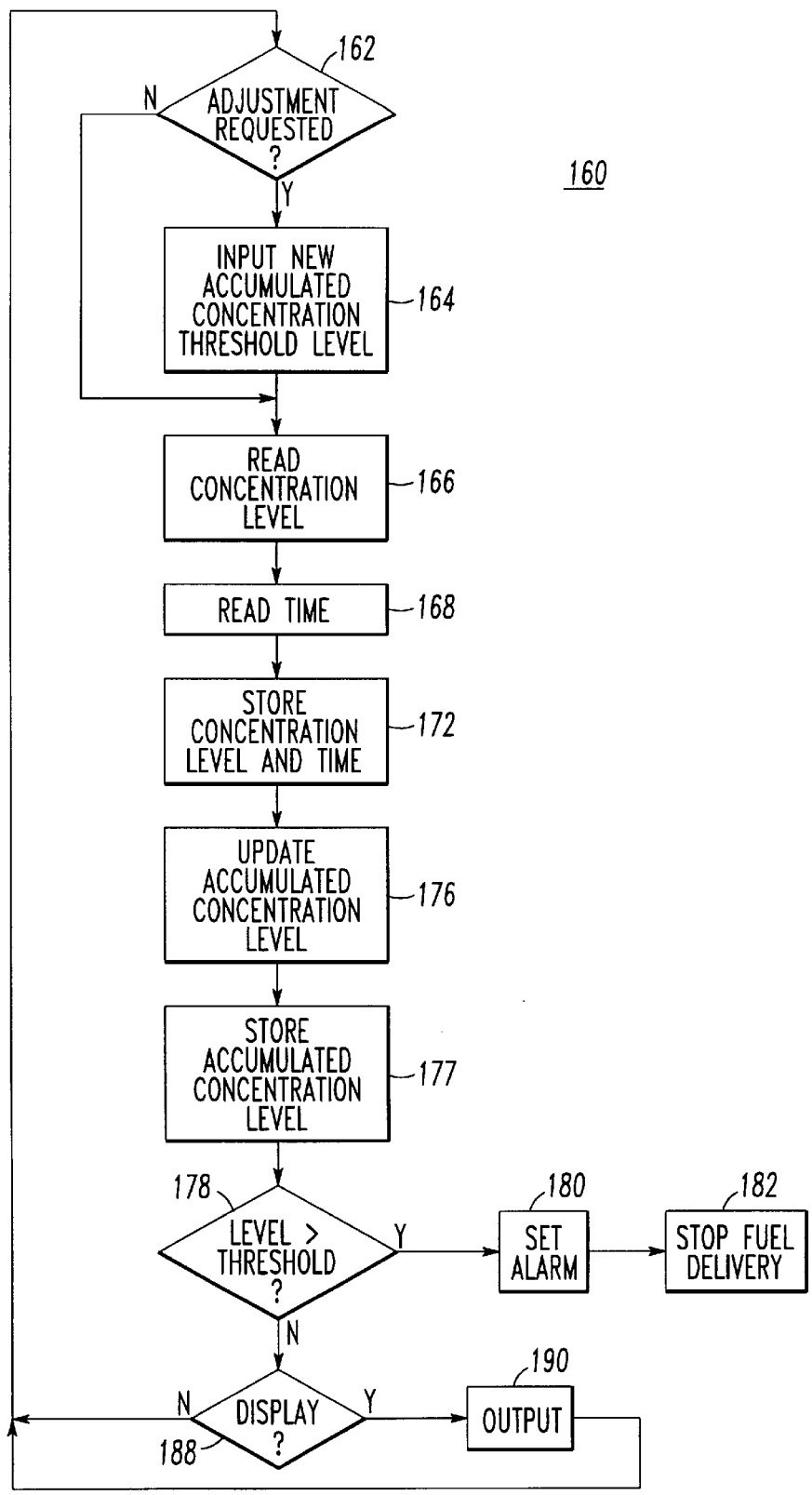
FIG. 5 is a flowchart of another embodiment of software suitable for execution by the control systems of FIGS. 2 and 3.

Referring to FIG. 5, an exemplary software routine 160 for execution by the control systems 106 and 140 of FIGS. 2 and 3, respectively, is illustrated. The routine 160 obtains a concentration level from the corresponding contaminant sensor, accumulates that concentration level, and, then, compares the accumulated concentration level (e.g., ppm-hours of ionized sodium in the combustion flame over time) with a predetermined or suitably adjusted threshold level (e.g., maximum allowed ppm-hours of ionized sodium). The result of the comparison is employed to determine whether to disable the corresponding fuel delivery system and, thus, arrest combustion.

For convenience of reference, the routine 160 of FIG. 5 is described with respect to the control system 140 of FIG. 3, although it is also applicable to the control system 106 of FIG. 2. Steps 162,164,166,178,180,182 of routine 160 generally correspond to the respective steps 148,150,152,154, 156,158 of routine 146 of FIG. 4. First, at 162, it is determined whether an adjustment of the accumulated concentration threshold level has been requested by the user. If so, at 164, the user suitably inputs a new accumulated concentration threshold (e.g., ACT of FIG. 3) level. Otherwise, if no adjustment was requested, and after 164, the concentration level 141 is read, at 166, from the flame spectrometer 128. The time of that reading is obtained, at 168, from a timer (T) 170. Then, at 172, the concentration level and time are stored in a suitable data storage such as exemplary memory (M) 174 (e.g., disk, RAM). Next, at 176, the accumulated concentration level is updated and then stored, at 177, in the memory 174.

For example, the accumulated concentration level may be calculated from the initial time of operation of the combustor 126, over any previous time period (e.g., one second, one minute, one hour, one day, one month, one year), or since a previous time (e.g., since 1:07 pm) and/or date. In this manner, an historical record of the accumulation of the concentration level 141 is updated and stored with respect to operating time of the combustor 126.

At 178, the accumulated contaminant concentration level is compared to the threshold level. If the accumulated concentration level exceeds the threshold level, then, at 180, an alarm is generated. Next, at 182, output signal 184 is set to close valve 186 and, thereby, stop delivery of the fuel 144. Otherwise, after 178, at 188, it is determined whether display of the accumulated concentration threshold level has been requested. If so, at 190, a suitable history of the accumulated concentration threshold level, concentration levels and/or time is output to display 192. Otherwise, if no output was requested, and after 190, execution resumes at 162.

As shown in FIG. 3, the display 192 is employed by the control system 140 to display the historical record of the accumulated contaminant concentration level over the operating life of the combustor 126. Although an exemplary accumulated concentration level is disclosed, other combustor variables (e.g., operating temperature, power output, load) may also be monitored, stored, displayed, and considered as part of the alarm logic.

The exemplary combustor fuel contaminant sensors of FIGS. 2 and 3 are employed to continuously sense the contaminant level of the respective combustors 100 and 126 in real-time. These systems have a relatively long useful life, a quick response time, and result in lower combustor repair costs and less frequent repairs. Since the detection of contaminants occurs during the combustion of fuel, all of the fuel must pass through the combustors and, thus, all of the fuel can, theoretically, be checked for the presence of sodium. By monitoring for sodium, and shutting off the fuel delivery system when sodium is detected, the risk of hot-section corrosion in gas turbine combustor exhaust is significantly reduced. Furthermore, continuous, real-time sensing protection may be incorporated into control logic to protect the combustor, without relying on laboratory results. This process is less expensive than other processes which employ a laboratory flame emission spectrometer.

Although the invention has been discussed with reference to a combustor for a gas turbine, the invention may be practiced with respect to combustors used in other types of machinery in which the detection of contaminants is desirable. For example, other combustors may employ different arrangements for delivery, such as a single manifold and a single fuel line, and/or mixing of fuel and a suitable oxidant, while still other combustors do not premix fuel and air. Other fuel delivery systems may employ a single fuel flow control valve to start, adjust, and/or stop the flow of fuel to the combustor. Still other combustors may employ different mechanisms to establish one or more combustion flames, and, thus, one or more contaminant sensors may be employed.

While for clarity of disclosure reference has been made herein to the exemplary display 192 for displaying an historical record of accumulation of concentration level of a fuel contaminant with respect to operating time of a combustor, it will be appreciated that the historical information may be stored, printed on hard copy, be computer modified, or be combined with other data. All such processing shall be deemed to fall within the terms "display" or "displaying" as employed herein.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. A combustor for burning fuel from a fuel supply, the fuel including a contaminant having a level, said combustor comprising:

a combustion chamber;

means for delivering the fuel to said combustion chamber;

means for establishing a combustion flame in said combustion chamber by burning the fuel;

at least one fuel line operatively connecting said means for delivering to the fuel supply;

means for sensing the level of said contaminant within the combustion flame; and means for disabling said means for delivering as a function of the level of said contaminant.

2. The combustor of claim 1 wherein said means for disabling includes means for generating an alarm as a function of the level of said contaminant; and means employing said alarm for disabling said means for delivering in order to stop delivery of the fuel to said combustion chamber.

3. The combustor of claim 2 wherein said means for generating an alarm includes means for comparing the level of said contaminant with a predetermined level.

4. The combustor of claim 2 wherein said means for generating an alarm includes means for comparing the level of said contaminant with an adjustable level.

5. The combustor of claim 2 wherein said means for disabling includes at least one fuel control valve installed in said at least one fuel line, respectively; and means for closing said at least one fuel control valve in order to stop delivery of the fuel to said combustion chamber.

6. The combustor of claim 1 wherein said contaminant is sodium; wherein said combustion flame includes ionized sodium; and wherein said means for sensing includes means for sensing the level of the ionized sodium in said combustion flame.

7. The combustor of claim 1 wherein said combustion flame has a spectrum; and wherein said means for sensing the level of said contaminant includes spectrometer means for monitoring the spectrum of the combustion flame.

8. The combustor of claim 7 wherein said combustion flame has a sodium "D" line emission; and wherein said spectrometer means includes means for detecting said sodium "D" line emission.

9. The combustor of claim 7 wherein said ionized sodium has a wavelength; and wherein said spectrometer means includes photo-detector means for detecting the wavelength of said ionized sodium.

10. The combustor of claim 1 wherein said means for sensing the level of said contaminant includes means for sensing said level in real-time.

11. The combustor of claim 1 wherein said means for sensing the level of said contaminant includes means for continuously sensing said level.

12. The combustor of claim 1 wherein said level is a concentration level of said contaminant.

13. The combustor of claim 1 wherein said level is an accumulation of a concentration level of said contaminant over time.

14. The combustor of claim 13 wherein said means for disabling includes means for storing the accumulation of the concentration level of said contaminant with respect to operating time of said combustor; and means for displaying said accumulation of the concentration level.

15. The combustor of claim 1 wherein said combustor is a gas turbine combustor.

16. A gas turbine combustor for burning fuel from a fuel supply, the fuel including a contaminant having a level, said gas turbine combustor comprising:

a combustion chamber;

means for delivering the fuel to said combustion chamber;

means for establishing a combustion flame having a combustion spectrum in said combustion chamber by burning the fuel with compressed air;

at least one fuel line operatively connecting said means for delivering to the fuel supply;

means employing the combustion spectrum of the combustion flame for sensing the level of said contaminant; and means for disabling said means for delivering as a function of the level of said contaminant.

17. The gas turbine combustor of claim 16 wherein said combustion chamber includes a plurality of flame detector ports and a flame detection system; and wherein said means employing the combustion spectrum of the combustion flame includes means for monitoring the combustion spectrum from one of said flame detector ports.

18. The gas turbine combustor of claim 16 wherein said means for disabling is integrated with a turbine control system.

19. A method for burning fuel including a contaminant in a combustor, said method comprising:

employing a combustion chamber;

delivering the fuel to said combustion chamber;

establishing a combustion flame in said combustion chamber by burning the fuel;

sensing a level of said contaminant within the combustion flame; and stopping delivery of the fuel to said combustion chamber as a function of the level of said contaminant.

20. The method of claim 19 further comprising:

employing a gas turbine combustor as said combustor;

establishing the combustion flame with a spectrum in said combustion chamber; and sensing the level of said contaminant from the spectrum of the combustion flame.

21. The method of claim 19 further comprising:

storing an historical record of an accumulation of a concentration level of said contaminant with respect to operating time of said combustor; and displaying said historical record.

* * * * *